(12) United States Patent
Opara et al.

(10) Patent No.: US 12,036,326 B2
(45) Date of Patent: Jul. 16, 2024

(54) METHOD OF ENCAPSULATING CELLS USING A MICROFLUIDIC ENCAPSULATION DEVICE

(71) Applicant: Wake Forest University Health Sciences, Winston-Salem, NC (US)

(72) Inventors: Emmanuel C. Opara, Durham, NC (US); Adam R. Hall, Clemmons, NC (US)

(73) Assignee: Wake Forest University Health Sciences, Winston-Salem, NC (US)

( * ) Notice: Subject to any disclaimer, the term of this patent is extended or adjusted under 35 U.S.C. 154(b) by 990 days.

(21) Appl. No.: 16/355,073

(22) Filed: Mar. 15, 2019

(65) Prior Publication Data

US 2019/0282510 A1  Sep. 19, 2019

Related U.S. Application Data

(60) Provisional application No. 62/644,720, filed on Mar. 19, 2018.

(51) Int. Cl.
| | |
|---|---|
| *C12N 5/00* | (2006.01) |
| *A61K 9/50* | (2006.01) |
| *B01L 3/00* | (2006.01) |
| *C12N 5/0775* | (2010.01) |
| *C12N 11/04* | (2006.01) |

(52) U.S. Cl.
CPC ...... *A61K 9/5036* (2013.01); *B01L 3/502761* (2013.01); *C12N 5/0012* (2013.01); *C12N 5/0663* (2013.01); *C12N 11/04* (2013.01)

(58) Field of Classification Search
CPC ............ A61K 9/5036; A61K 2035/128; C12N 5/0012; C12N 11/04; C12M 25/16; B01F 33/3011
See application file for complete search history.

(56) References Cited

U.S. PATENT DOCUMENTS

| | | | |
|---|---|---|---|
| 7,595,195 B2 | 9/2009 | Lee et al. | |
| 7,759,111 B2 | 7/2010 | Lee et al. | |
| 2014/0127290 A1* | 5/2014 | He | A61K 9/5036 435/178 |
| 2017/0199173 A1* | 7/2017 | Konry | C12M 25/01 |

OTHER PUBLICATIONS

Utech et al. Microfluidic Generation of Monodisperse, Structurally Homogeneous Alginate Microgels for Cell Encapsulation and 3D Cell Culture; Advanced Healthcare Materials, vol. 4, pp. 1628-1633. (Year: 2015).*
Chen et al. Microfluidic One-Step Synthesis of Alginate Microspheres Immobilized With Antibodies; Journal of the Royal Society Interface; vol. 10, pp. 1-8. (Year: 2013).*
Sugiura et al. Diameter Control of Calcium Alginate Beads Using Microfabricated Nozzle Array; In Asian Pacific Confederation of Chemical Engineering congress program and abstracts Asian Pacific Confederation of Chemical Engineers congress program and abstracts, pp. 1-7. (Year: 2004).*
Moyer et al. Alginate Microencapsulation Technology for the Percutaneous Delivery of Adipose Derived Stem Cells; Transplantation Surgery and Research, vol. 65, No. 5, pp. 497-503. (Year: 2010).*
Swioklo et al. Process Parameters for the High Scale Production of Alginate Encapsulated Stem Cells for Storage and Distribution Throughout the Cell Therapy Cupply Chain; Process Biochemistry, vol. 59, pp. 289-296. (Year: 2017).*
Chavarri et al. Encapsulation Technology to Protect Probiotic Bacteria; Chapter 23, Rigobelo, E (ed.). 2012, Probiotics, IntechOpen, London, pp. 501-540. (Year: 2012).*
Ma et al. Chondrogenesis of Human Mesenchymal Stem Cells Encapsulated in Alginate Beads; Journal of Biomedical Materials Research Part A, vol. 64, No. 2, pp. 273-281. (Year: 2003).*
Sharma et al., "Microfluidic Approach to Cell Microencapsulation", Methods Mol. Biol., vol. 1479, 2017, pp. 71-76.
Tendulkar et al., "A three-dimensional microfluidic approach to scaling up microencapsulation of cells", Biomed Microdevices, vol. 14, No. 3, Jun. 2012, pp. 461-469.
Trivedi et al., "Microfluidic Encapsulation of Cells in Alginate Capsules for High Throughput Screening", 31st Annual International Conference of the IEEE Engineering in Medicine and Biology Society, Minneapolis, MN, Sep. 2-6, 2009, pp. 7037-7040.
Headen et al., "Microfluidic-Based Generation of Size-Controlled, Biofunctionalized Synthetic Polymer Microgels for Cell Encapsulation", Adv. Mater, vol. 26, No. 16, May 2014, pp. 303-3008.
Enck et al., Abstract—"A Novel Microfluidic Encapsulation Device for Treatment of Type 1 Diabetes", 2017 Conference of the North Carolina Tissue Engineering and Regenerative Medicine Society, 1 p.

* cited by examiner

*Primary Examiner* — Jeanette M Lieb
*Assistant Examiner* — Paul C Martin
(74) *Attorney, Agent, or Firm* — Myers Bigel, P.A.

(57) ABSTRACT

The present disclosure describes a method of encapsulating cells in a crosslinked alginate microbead using a microfluidic encapsulation device.

14 Claims, 7 Drawing Sheets

METHOD OF ENCAPSULATING CELLS USING A MICROFLUIDIC ENCAPSULATION DEVICE

STATEMENT OF PRIORITY

This application claims the benefit, under 35 U.S.C. § 119(e), of U.S. Provisional Application Ser. No. 62/644,720, filed Mar. 19, 2018, the entire contents of which is incorporated by reference herein.

FIELD

The invention relates to a method of encapsulating cells using a microfluidic encapsulation device.

BACKGROUND

Microencapsulation has been a prominent staple in regenerative medicine for the past few decades. It allows for immobilization, immune protection, and controlled release of therapeutics. For diabetes treatment, alginate has been the most common biomaterial used to encapsulate islets for allogenic delivery. Current methods for encapsulation use dripping methods, which take advantage of air, and gravity to form microbeads. However, these technologies form beads with large polydispersity which could lead to a variable number of cells in each head, as well as stress marks on the beads due to interaction of microbeads with parts of the encapsulating devices. Improved methods for encapsulation of cells are needed.

SUMMARY

The present invention is directed to a method of encapsulating cells (e.g., stem cells) cells) using a microfluidic encapsulation device that comprises a first, second, and third flow line. The second flow line junctions with the first flow line at a first-second flow line junction, and the third flow line junctions with the first flow line at a first-third flow line junction at a point after the first-second flow line junction. The method comprises flowing an aqueous solution through the first flow line, the aqueous solution comprising the cells, alginate, and a divalent cation (e.g., a chelated divalent cation); providing a first non-aqueous liquid that flows through the second flow line, the first non-aqueous liquid being immiscible with the aqueous solution; providing a second non-aqueous liquid comprising an acid that flows through the third flow line, the second non-aqueous liquid being immiscible with the aqueous solution; forming an alginate microbead by cutting off the flowing of the aqueous solution with the first non-aqueous liquid at the first-second flow line junction; then lowering a surface pH of the alginate microbead with the second non-aqueous liquid at the first-third flow line junction to initiate crosslinking with the divalent cation and form a crosslinked alginate microbead, thereby encapsulating the cells with crosslinked alginate.

It is noted that aspects of the invention described with respect to one embodiment, may be incorporated in a different embodiment although not specifically described relative thereto. That is, all embodiments and/or features of any embodiment can be combined in any way and/or combination. Applicant reserves the right to change any originally filed claim and/or file any new claim accordingly, including the right to be able to amend any originally filed claim to depend from and/or incorporate any feature of any other claim or claims although not originally claimed in that manner. These and other objects and/or aspects of the present invention are explained in detail in the specification set forth below. Further features, advantages and details of the present invention will be appreciated by those of ordinary skill in the art from a reading of the figures and the detailed description of the preferred embodiments that follow, such description being merely illustrative of the present invention.

DETAILED DESCRIPTION

The present invention now is described more fully hereinafter with reference to the accompanying drawings, in which embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art.

The present invention now will be described more fully hereinafter with reference to the accompanying drawings, in which illustrative embodiments of the invention are shown. Like numbers refer to like elements and different embodiments of like elements can be designated using a different number of superscript indicator apostrophes (e.g., 10, 10', 10").

In the figures, certain layers, components or features may be exaggerated for clarity, and broken lines illustrate optional features or operations unless specified otherwise. This invention may, however, be embodied in many different forms and should not be construed as limited to the embodiments set forth herein; rather, these embodiments are provided so that this disclosure will be thorough and complete, and will fully convey the scope of the invention to those skilled in the art.

It will be understood that, although the terms first, second, etc. may be used herein to describe various elements, components, regions, layers and/or sections, these elements, components, regions, layers and/or sections should not be limited by these terms. These terms are only used to distinguish one element, component, region, layer or section from another region, layer or section. Thus, a first element, component, region, layer or section discussed below could be termed a second element, component, region, layer or section without departing from the teachings of the present invention. The sequence of operations (or steps) is not limited to the order presented in the claims or figures unless specifically indicated otherwise.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein. Well-known functions or constructions may not be described in detail for brevity and/or clarity.

The terminology used herein is for the purpose of describing particular embodiments only and is not intended to be limiting of the invention. As used herein, the singular forms "a", "an" and "the" are intended to include the plural forms, as well, unless the context clearly indicates otherwise. It will be further understood that the terms "comprises" and/or "comprising", when used in this specification, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. The term "about" refers to numbers in a range of +/−20% of the noted value.

Figure 1A:
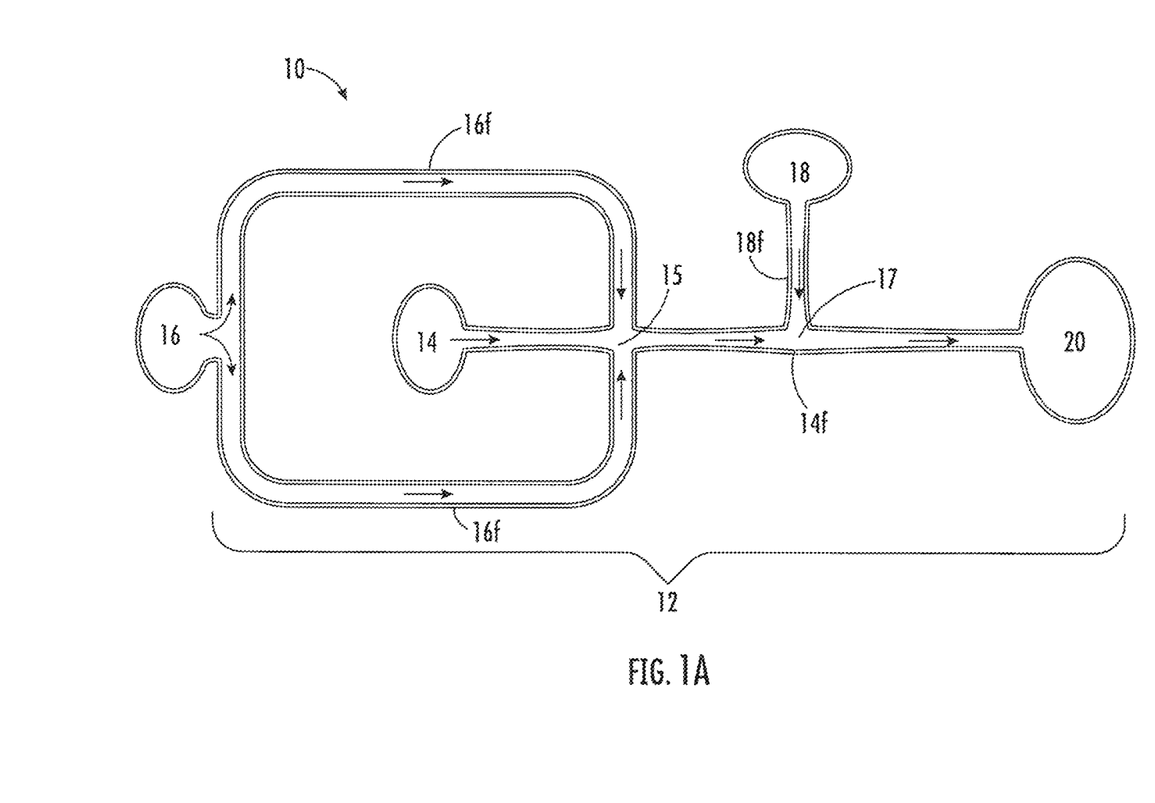
FIG. 1A is a schematic illustration of an example system of encapsulating cells using a microfluidic encapsulation device according to embodiments of the present invention.

Referring now to the figures, FIG. 1A shows a schematic illustration of an example system 10 using a microfluidic encapsulation device 12 for encapsulating cells according to embodiments of the present invention. The system 10 generally includes a microfluidic encapsulation device 12 comprising a series of intersecting components. For example, the microfluidic encapsulation device 12 of the system 10 may have a series of chambers (14, 16, 18, 20), each chamber being coupled to a flow line (14f, 16f, 18f).

Figure 1B:
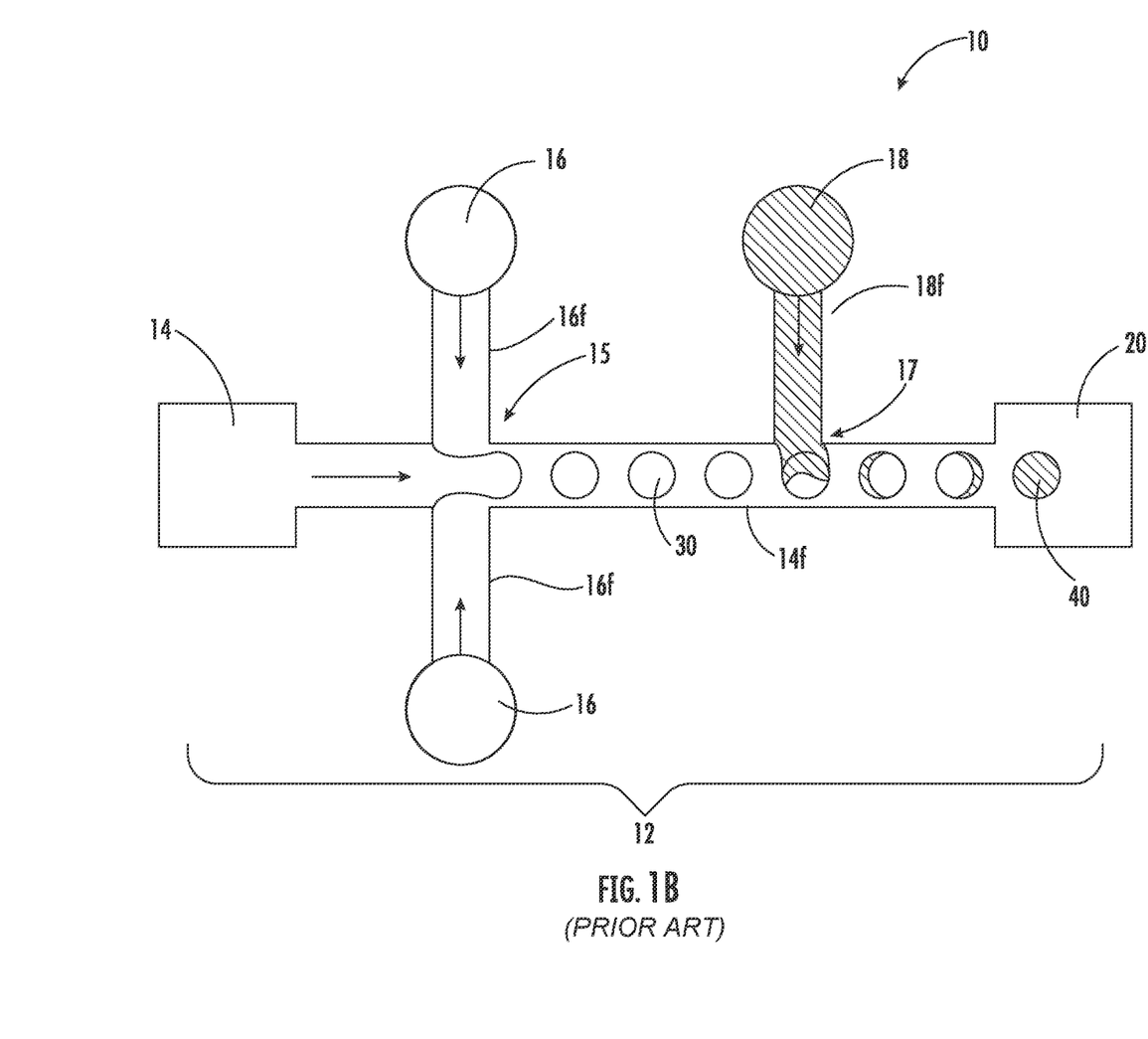
FIG. 1B is a schematic illustration of an example system of encapsulating cells using a microfluidic encapsulation device according to embodiments of the present invention.

As illustrated in FIGS. 1A and 1B, in some embodiments, the microfluidic encapsulation device may have four chambers (a first chamber 14, a second chamber 16, a third chamber 18, and a collection chamber 20) and three flow lines (a first flow line 14f, a second flow line 16f, and a third flow line 18f). The first flow line 14f may be coupled to and extend from the first chamber 14. The first flow line 14f may extend through the microfluidic encapsulation device 12 from the first chamber 14 to the collection chamber 20. The second flow line 16f may be coupled to and extend from the second chamber 16. The third flow line 18f may be coupled to and extend from the third chamber 18.

In some embodiments, the microfluidic encapsulation device 12 may have more than one second chamber 16 (FIG. 1B). In the embodiments when the microfluidic encapsulation device 12 has more than one second chamber 16, additional second flow lines 16f may be coupled to and extend from each second chamber 16.

In some embodiments, the second flow line(s) 16f of the microfluidic encapsulation device 12 may orthogonally intersect or junction the first flow line 14f (i.e., the first-second junction 15). In some embodiments, the third flow line 18f may intersect or junction the first flow line 14f (i.e., the first-third junction 17). The first-third junction 17 may occur at a point along the first flow line 14f after the first-second junction 15.

In some embodiments, the first chamber 14 may contain an aqueous solution. A single stream of the aqueous solution may flow from the first chamber 14 through the first flow line 14f. The aqueous solution may flow through the first flow line 14f at a flow rate of about 50 µL/hr to about 400 µL/hr.

In some embodiments, the aqueous solution contained in the first chamber 14 and flowing through the first flow line 14f may comprise an alginate, cells and a divalent cation. An example alginate that may be used is PRONOVA™ UP LVM (NovaMatrix). In some embodiments, the cells may be stem cells. In some embodiments, the divalent cation may be calcium, strontium, or barium. In some embodiments, the aqueous solution comprises alginate mixed (e.g., homogeneously mixed) with a chelated divalent cation such as calcium-ethylenediaminetetraacetic acid (EDTA) and stem cells. As an example, in some embodiments, a solution of calcium chloride (e.g., 100 mM) may be mixed with a solution of disodium-EDTA (e.g., 100 mM) to form a solution (e.g., a 50 mM solution). Using a base, such as sodium hydroxide (NaOH), the pH of the solution can be adjusted to about 7. The solution may then be mixed with alginate (e.g., 1.5% by weight) to form an aqueous alginate solution. Cells can be suspended in this solution, e.g., at a concentration of about 5, 10, 12, 15 or 20 million cells/mL. This concentration may vary depending on desired amount of cells/bead (e.g., about 1, 5, 10, 15, 20, 25, 30, 35, 40, or 45 cells/bead on average). For example, in some embodiments a concentration of about 10 million cells/mL can generate about 30 cells/bead on average.

In some embodiments, the second chamber 16 may contain a non-aqueous liquid. The non-aqueous liquid may flow from the second chamber 16 through the second flow line 16f. The non-aqueous liquid may be immiscible with the aqueous solution flowing through the first flow line 14f from the first chamber 14. Immiscible liquids, as known in the art, are generally resistant or incapable of being mixed or blended together, for example, oil and water are immiscible. In some embodiments, the non-aqueous liquid may flow through the second flow line 16f at a flow rate of about 3 or 5 mL/hr and about 15 mL/hr.

In some embodiments, the non-aqueous liquid flowing through the second flow line 16f may comprise a hydrophobic liquid, such as mineral oil, and/or optionally a surfactant. In some embodiments, the non-aqueous liquid may comprise from about 0.5% to about 4.5% surfactant, typically from about 0.5% to about 1.5% surfactant. As an example, the non-aqueous liquid flowing through the second flow line 16f may comprise about 96% mineral oil and about 4% surfactant.

In some embodiments, the surfactant may be a non-ionic surfactant. An example of a non-ionic, surfactant that may be used is Span® 80 (MilliporeSigma, St. Louis, MO.). To evenly distribute the surfactant, in some embodiments, the non-aqueous liquid may be vortexed before use in the encapsulation device.

In some embodiments, the third chamber 18 may contain a second non-aqueous liquid. The second non-aqueous liquid may flow from the third chamber 18 through the third flow line 18f. The second non-aqueous liquid flowing through the third flow line 18f may be a different non-aqueous liquid than the non-aqueous liquid flowing through the second flow line 16f. In some embodiments, the second non-aqueous liquid may flow through the third flow line 18f at a flow rate from about 4 mL/hr to about 8 mL/hr.

In some embodiments, the second non-aqueous liquid flowing through the third flow flow line 18f may comprise a hydrophobic liquid, such as mineral oil, and an acid. In some embodiments, the second non-aqueous liquid may comprise about 0.5% to about 1.5% acid (e.g., acetic acid). For example, the second non-aqueous liquid flowing through the third flow line 18f may comprise about 98.6% mineral oil and about 1.4% acetic acid. The second non-aqueous liquid may be vortexed to evenly distribute the acid before use in the device.

Referring to FIG. 1B, in some embodiments, an aqueous solution comprising an alginate, cells, and a divalent cation flows from the first chamber 14 through the first flow line 14f. A first non-aqueous liquid that is immiscible with the aqueous solution flows through the second flow lines 16f from two second chambers 16 forming beads (e.g., microbeads) at the first-second junction 15. A second non-aqueous liquid that is also immiscible with the aqueous solution flows through the third flow line 18f from the third chamber 18 contacting the beads as they flow along the first flow line 14f.

As a single stream of the aqueous solution flows through first flow line 14f, two orthogonal streams of the first non-aqueous liquid flow through the second flow lines 16f. The single stream of the aqueous solution contacts the two orthogonal streams of the first non-aqueous liquid at the first-second junction 15. Shear forces induced by the opposing streams of the first non-aqueous liquid at the first-second junction 15, in addition to the immiscibility of the first non-aqueous liquid and the aqueous solution, can cause the flow of the single stream of the aqueous solution to be cut off resulting in the formation of an alginate microbead 30 (FIGS. 1B and 1C).

As discussed in further detail below, in some embodiments, adjusting the flow rate of the first non-aqueous liquid through the second flow line(s) 16f may affect the diameter of the formed alginate microbeads 30. For example, increasing the flow rate of the first non-aqueous liquid through the second flow line(s) 16f may decrease the diameter of the formed alginate microbeads 30, or vice versa.

Figure 1C:
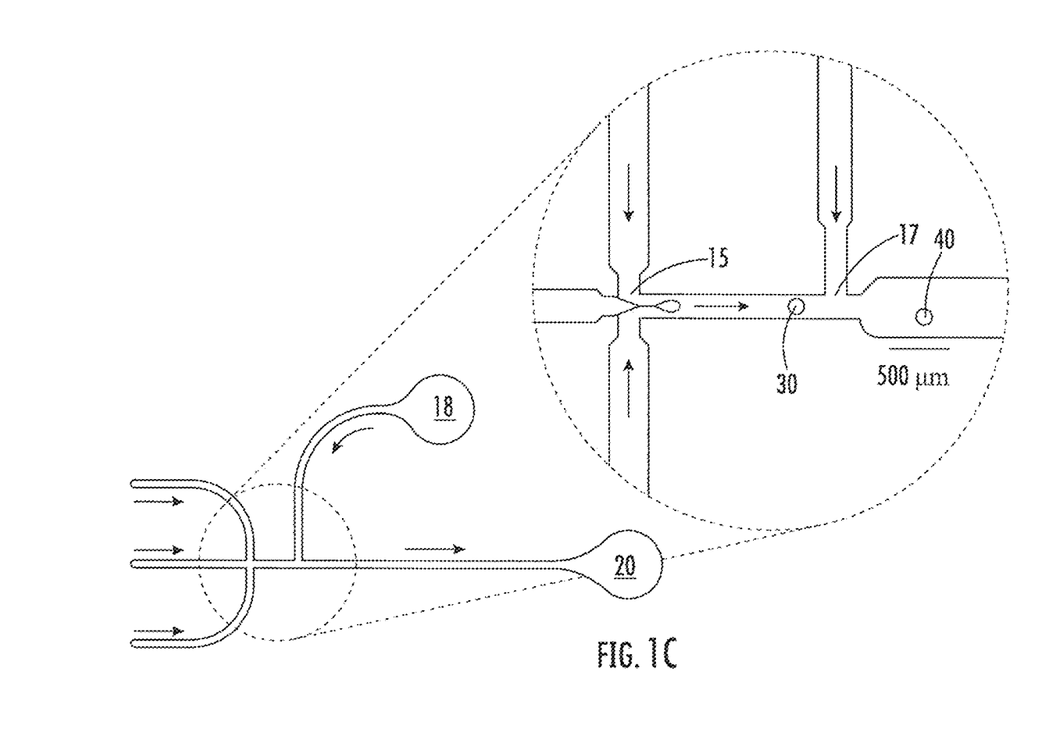
FIG. 1C is an enlarged view of a section of the example system illustrated in FIGS. 1A and 1B.

As shown in FIGS. 1B and 1C, the formed alginate microbead 30 continues to flow through the first flow line 14f as the second non-aqueous liquid flows into the system 10 at the first-third junction 17. When the second non-aqueous liquid containing acid is contacted to the alginate microbead 30, the pH at the surface of the alginate microbead 30 may be lowered. Lowering the pH at the surface of the alginate microbead 30 can initiate crosslinking of alginate components of the second non-aqueous liquid with the divalent cation mixed in the aqueous solution.

In some embodiments, encapsulating stem cells in the crosslinked alginate microbeads as described above may result in reduced proliferation allowing for accurate dosing of stem cells for therapeutic effects.

Figure 3A:
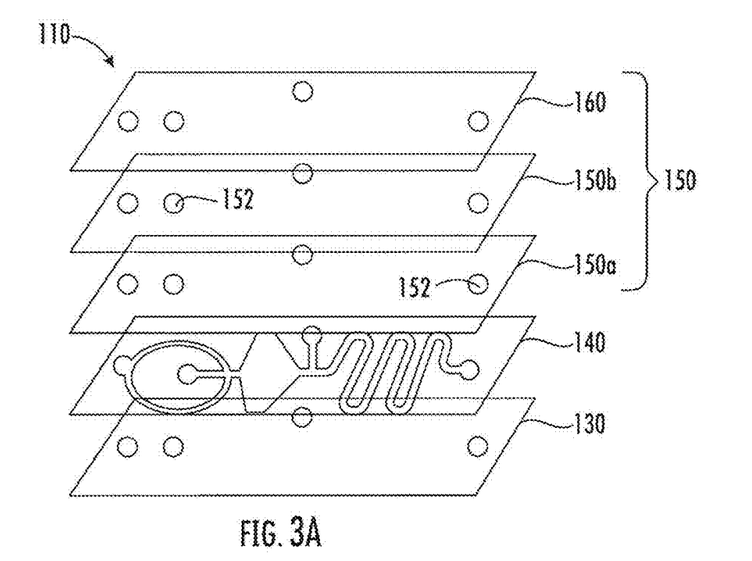
FIGS. 3A and 3B show another example system of encapsulating cells using a microfluidic encapsulation device according to embodiments of the present invention. The left insert of FIG. 3B is a microscopic image showing microbead formation. The scale bar in FIG. 3B is 150 µm. The right insert of FIG. 3B shows the pH of the oil drops once it is mixed with the acetic acid mineral oil. The drop in pH causes the EDTA to release $Ca^{2+}$ from within the microbead, thus crosslinking it homogenously and forming a crosslinked microbead.
Figure 3B:
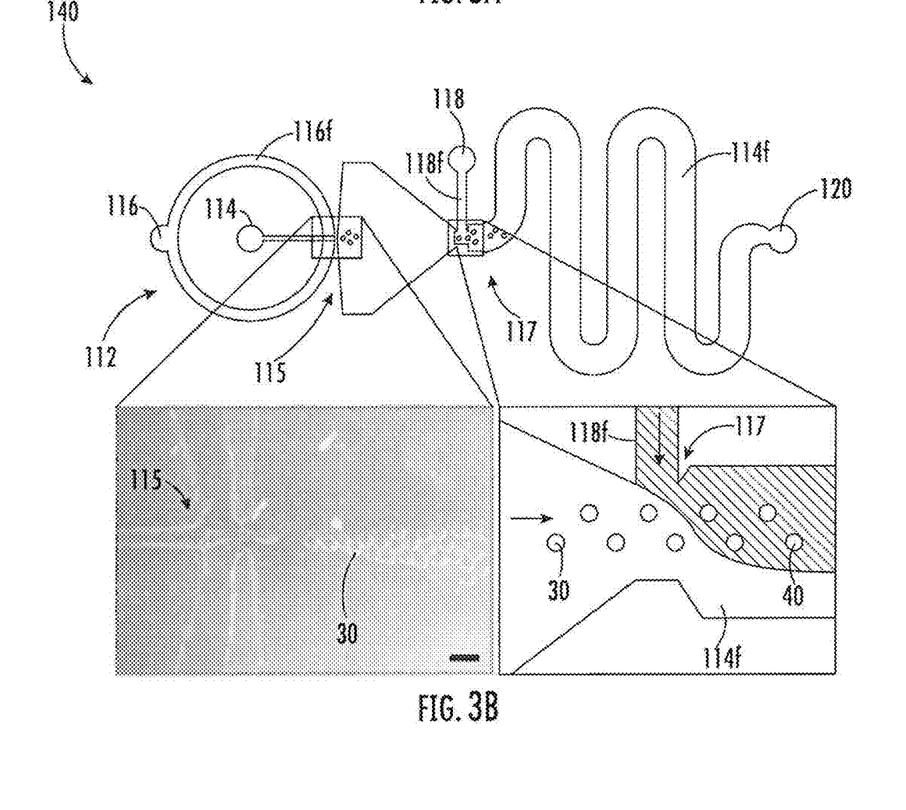

Referring now to FIGS. 3A and 3B, another example system 110 of encapsulating cells using a microfluidic encapsulation device 112 according to embodiments of the present invention is illustrated. FIG. 3A shows a layered view of a microfluidic encapsulation device 112. In some embodiments, the device 112 may comprise four layers: a glass layer 130, a microfluidic layer 140, a lid 150 (featuring inlets/outlets 152), and a top layer 160 which may help prevent leaking out of the inlets 152.

In some embodiments, the microfluidic layer 140 may comprise a patterned adhesive film that may be attached to a glass microscope slide 130. In some embodiments, the lid 150 may comprise a poly(methyl methacrylate) (PMMA) sheet 150a, a polydimethylsioxane (PDMS) layer 160 and one or more adhesive film layers 150b. The PMMA sheet 150a may be attached to one of the adhesive film 150 and subsequently sealed to the bottom surface of the top layer 160. In some embodiments, the PMMA sheet 150a may be sealed to the PDMS layer 160 using air plasma bonding. The PDMS layer 160 forms a tight junction with the tubing (e.g., polytetrafluoroethylene tubing that may be inserted into each inlet/outlet 152 for fluid delivery) to prevent leakage. The second adhesive film 150b may be attached to the bottom of the PMMA sheet 150a. The entire structure 150/160 may then be placed on the top surface of the patterned microfluidic layer 140 to form the microfluidic encapsulation device 112.

FIG. 3B shows the microfluidic layer 140 of the microfluidic encapsulation device 112 in more detail. The device 112 may comprise a first immiscible liquid inlet 116, an aqueous liquid inlet 114, an acetic acid/mineral oil inlet 118, and a collection outlet 120. See also Example 2 below.

In some embodiments, when initially formed, the alginate microbead 30 typically has a neutral pH, such as from about 7.0 to about 7.6. To initiate crosslinking with a divalent cation, the pH of the alginate microbead is lowered (e.g., to about 5.0). Under neutral conditions, calcium ions can be sequestered by EDTA. When the pH of the alginate microbeads drops to about 5.0, the EDTA can release the calcium ions, allowing them to freely crosslink the alginate chains.

As a result of the crosslinking, a crosslinked alginate microbead 40 can be formed encapsulating the cells. The crosslinked alginate microbead 40 can be a gelatinous structure that prevents the cells from migrating outside of the crosslinked alginate microbead 40 and/or reduces cell proliferation.

In some embodiments, the crosslinked alginate microbeads 40 with the encapsulated cells continue to flow through the first flow line 14f. The crosslinked alginate microbeads 40 can then be collected in the collection chamber 20.

In some embodiments, after being collected in the collection chamber 20, the crosslinked alginate microbeads 40 may be washed. In some embodiments, the crosslinked alginate microbeads 40 may be washed with an organic wash liquid (e.g., hexane) and/or an aqueous wash liquid (e.g., a salt or saline solution). In some embodiments, the aqueous wash liquid may comprise a calcium supplemented physiological salt solution. Note that the calcium solution should not be hypotonic compared to the calcium in the microbeads, otherwise the calcium in the microbeads may diffuse out causing an un-crosslinking. A wash solution with a pH indicator dye such as Phenol Red can be helpful as a visual aid to monitor raising the pH of the crosslinked alginate microbeads back to neutral to promote cell survival.

In some embodiments, the formed crosslinked alginate microbeads 40 may have a diameter of about 80 μm and about 180 μm. This diameter range may vary but can be sized to allow the crosslinked alginate microbeads 40 to be directly implanted into the pancreas of a human without induction of pancreatitis (i.e., having a diameter less than 250 μm).

Bead size may be controlled by water fraction $W_f$, defined as:

$$W_f = \frac{V_W}{(V_W + V_O)} \qquad \text{Equation 1}$$

where $V_w$ is the volumetric flow rate of the aqueous alginate) stream and $V_O$ is that of the carrier fluid. The alginate and oil flow rates (e.g., through the first flow line 14*f* and second flow line 16*f*, respectively) may determine the size of the microbeads 40. For example, as alginate flow rate increased, so does the size of the droplets, and as the oil flow rate increased, the droplets are formed at a faster rate, which may lead to a decrease in size.

Alginate microbead size and shape were determined by analysis of bright-field optical images. The four parameters that were calculated were area, perimeter, circularity, and aspect ratio. Area A and perimeter P were determined directly via measurements performed using ImageJ software. Circularity C was calculated by the following equations:

$$C = 4\pi \left( \frac{A}{P^2} \right) \qquad \text{Equation 2}$$

Aspect ratio was calculated as the ratio of the major axis to the minor axis of the microbead. The closer that both circularity and aspect ratio were to 1.0, the more perfectly spherical the microbead is.

In some embodiments, the cells to be encapsulated, may be stem cells, such as mesenchymal stem cells (e.g., derived from bone marrow, umbilical cord tissue, adipose tissue, etc.). In some embodiments, when encapsulated within the crosslinked alginate microbead 40, the viability of the mesenchymal stem cells can be about 1 day to at least 28 days or more. In some embodiments, the encapsulated mesenchymal stem cells may have therapeutic effects for treatment of Type 1 diabetes.

In some embodiments, adjusting the flow rate of the aqueous solution through the first first flow line 14*f* may affect the rate of production and/or the polydispersity of the crosslinked alginate microbeads 40. In some embodiments, the crosslinked alginate microbeads 40 can be formed at a rate of production of from about 100 beads/min to about 1000 beads/min. In some embodiments, the crosslinked alginate microbeads 40 may have a polydispersity with a coefficient of variance from about 9% and about 15%. The coefficient of variance (CV) is the ratio of standard deviation to mean diameter and may be used as a metric of monodispersity of the crosslinked alginate microbeads 40. Generally, a population is considered to be monodisperse when the CV is less than 5%. In some embodiments, the method of the present invention may be able to achieve a mondispersity having a CV between about 2% and about 6%. Flow rates and diameters of flow lines may be varied based on the desired design of the microfluidic device, which can, in turn result in various bead sizes and/or rates of production.

The present subject matter will be now be described more fully hereinafter with reference to the accompanying EXAMPLES, in which representative embodiments of the presently disclosed subject matter are shown. The presently disclosed subject matter can, however, be embodied in different forms and should not be construed as limited to the embodiments set forth herein. Rather, these embodiments are provided so that this disclosure will be thorough and complete, and will fully convey the scope of the presently disclosed subject matter to those skilled in the art.

EXAMPLES

The following EXAMPLES provide illustrative embodiments. Certain aspects of the following EXAMPLES are disclosed in terms of techniques and procedures found or contemplated by the present inventors to work well in the practice of the embodiments. In light of the present disclosure and the general level of skill in the art, those of skill will appreciate that the following EXAMPLES are intended to be exemplary only and that numerous changes, modifications, and alterations can be employed without departing from the scope of the presently claimed subject matter.

Example 1

Material and Methods. Microfluidic devices are made by layering standard histology glass slides, double sided adhesive film, and polystyrene slides. The microfluidic device has three entry points with one collection line. Line A (16*f*) contains mineral oil with 4% Span 80. Line B (14*f*) contains alginate homogenously mixed with calcium-EDTA and mesenchymal stem cells (MSCs). The A-B junction (15) forms the beads by cutting off the flow of alginate with the entering mineral oil. Line C (18*f*) contains mineral oil with 1.4% acetic acid to lower the pH for crosslinking with calcium. The crosslinked beads are then collected (20), and washed first using Hexane and then Hank's Balanced Salt Solution. To reduce potential pressure that may be exerted on the pancreas during implantation, the target microbead size range was from 80 μm to 180 μm in diameter. After optimizing the device, MSCs were encapsulated and cell viability was tested on days 0, 4, 7, 14, 21, and 28 using a CFDA/PI live-dead stain.

A solution of 100 mM calcium chloride is mixed with a solution of 100 mM disodium-EDTA to make a 50 mM mixture. The pH is adjusted to 7 with NaOH. The solution is then mixed with alginate (1.5% wt LVM, Novamatrix) overnight to form an aqueous alginate solution. MSCs can be suspended in this mixture at a concentration of about 15 million cells/mL. This can concentration can vary depending on desired amount of cells/bead. This concentration generated about 30 cells/bead.

Figure 2A:
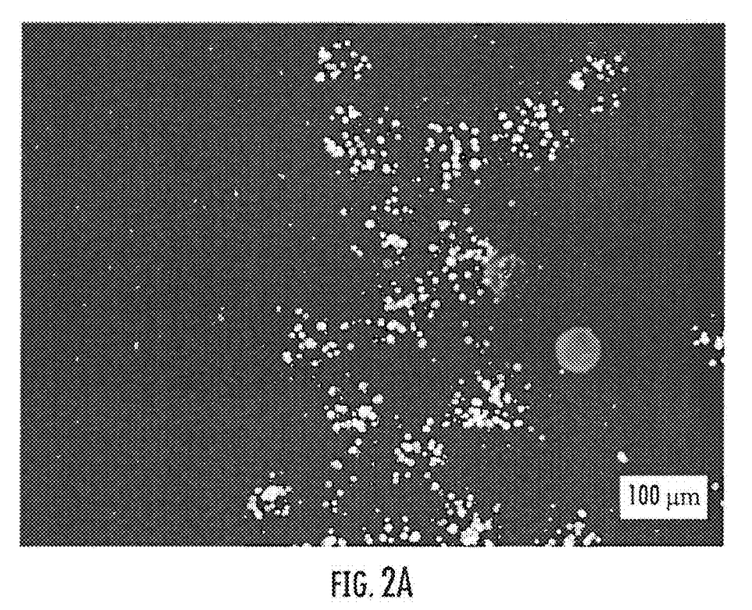
FIG. 2A is a microscopic image showing encapsulated mesenchymal stem cells at 7 days after encapsulation.
Figure 2B:
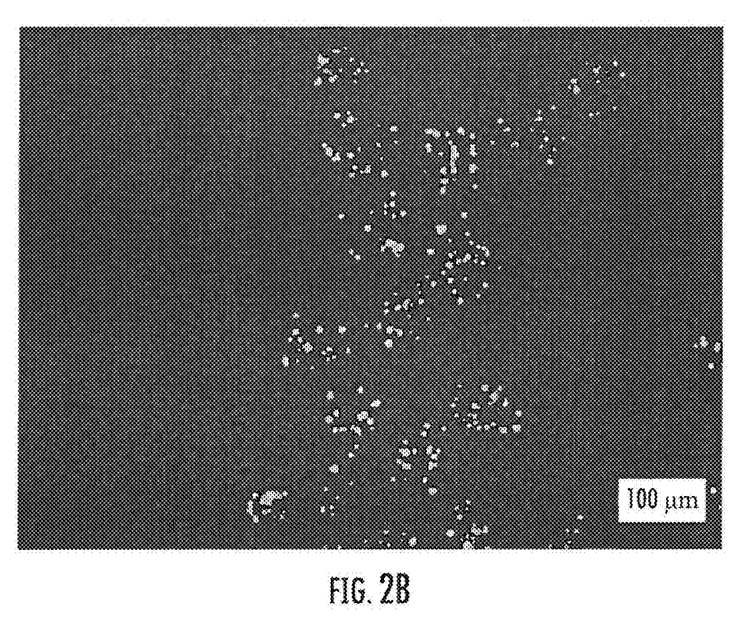
FIG. 2B is a microscopic image showing the corresponding live-dead stain of the encapsulated mesenchymal stem cells shown in FIG. 2A.

Results and Discussion. Increasing the flow rate of mineral oil, decreased the diameter of the microbeads, and changing the alginate flow rate affected the rate of production and monodispersity of the bead sizes. By adjusting flow rates, polydispersity was reduced to a coefficient of variance as low as 9.45%. Referring now to FIGS. 2A and 2B, encapsulating stem cells in the crosslinked alginate microbeads as described above may result in reduced proliferation allowing for accurate dosing of stem cells for therapeutic effects. For example, FIG. 2A is a microscopic image showing encapsulated mesenchymal stem cells at 7 days after encapsulation, FIG. 2B is a microscopic image showing the corresponding live-dead stain of the encapsulated mesenchymal stem cells shown in FIG. 2A. Live-dead stains immediately after encapsulation demonstrated that the microfluidic device did not harm the cells. Viability was maintained in culture for 28 days until the conclusion of the study.

Conclusion. The microfluidic device enabled the generation of spherical microbeads ii the desired range by adjusting the flow rates of mineral oil and alginate. The lack of proliferation in the encapsulated cells allows for accurate dosing of MSCs for therapeutic effects, and suggests that the integrity of the alginate bead will not be compromised by expansion once implanted into the pancreas, such as for treatment of autoimmune Type 1 diabetes.

Example 2

Materials and Methods

Reagents and Materials. The nonpolar (i.e., immiscible with water) carrier fluid was made by mixing mineral oil with 1% (v/v) Tween-80 (P4780, Sigma-Aldrich). 100 mM $CaCl_2$ (C77, Fisher Scientific) was mixed with equal, volume of 100 mM Ethylenediaminetetraacetic acid (EDTA) (E-5134, Sigma-Aldrich) to form a 50 mM Ca-EDTA solution. Ultrapure alginate (BP-1312-29, Novamatrix, Denmark) was made in a 1.5% (w/v) solution with the 50 mM Ca-EDTA solution. This solution was kept on ice prior to use. The nonpolar crosslinking fluid was made by mixing mineral oil with 1.4% (v/v) acetic acid (0714, Amresco).

Device Fabrication. The microfluidic device was fabricated by low-cost, rapid prototyping using a patterned laser cutting technique. The system consists of four layers: a glass base, the microfluidic layer, a lid featuring inlets/outlets, and a PDMS layer that prevents leaking out of the inlets (FIG. 3A). The microfluidic layer compromises patterned adhesive film (9495MPF, 3M, Minneapolis, MN) attached to a glass microscope slide. Channel thickness could be varied up to several millimeters using multiple patterned adhesive film layers, but for this report, all devices consisted of a single 100 μm thick layer. Microfluidic chambers were then formed in the adhesive film by $CO_2$ laser cutting (Full Spectrum, Las Vegas, NV) using a CAD file for pattern definition. The lid consisted of a 3 mm PMMA sheet (McMaster-Can, Douglasville, GA.), a 4 mm thick PDMS layer (10:1 Sylgard 184, Dow Corning Corporation, Midland, MI), and two adhesive films. Inlets and outlets were formed with a 20G blunt needle (PDMS) and $CO_2$ laser cutting (PMMA and adhesive films). The top PMMA surface was attached to one adhesive film and subsequently sealed to the bottom surface of the PDMS using air plasma bonding. The remaining adhesive film was attached to the bottom surface of the PMMA and the entire structure was placed on the top surface of the patterned microfluidic layer to form the microfluidic device. The resulting device was sealed by applying even pressure and polytetrafluoroethylene (PTFE, Cole-Partner, Vernon Hills, IL) tubing was inserted into each port for fluid delivery.

Microbead Formation. FIG. 3B shows an example microfluidic device having three inlet ports (114, 116, and 118) and one outlet (120). The mineral oil carrier and crosslinking fluids were pumped through inlets (114) and (118), respectively, using a microfluidic syringe pump (Braintree Scientific, Braintree, MA). Once the chambers were filled with oil, the 1.5% Alginate-Ca-EDTA solution was pumped through inlet (116), forming droplets upon contact with the immiscible mineral oil flowing from inlet (114) (FIG. 3B, left inset). Further downstream in the chamber, the droplets became crosslinked due to a decrease in pH induced by the acetic acid-mineral oil mixture (FIG. 3B, right inset). The ensuing sinusoidal segment of the chamber promoted full mixing of the carrier and crosslinking oil mixtures. The microbeads were collected in a 50 mL conical tube connected to the (120) port by tubing. Excess oil was aspirated from the solution before washing with hexane three times, letting the beads settle each time before aspirating and adding fresh hexane to the microbead pellet. The hexane was used to dissolve the residual mineral oil, allowing for effective transfer from the organic oil to aqueous media. Three additional washes of 100 mM $CaCl_2$ followed the hexane washes to ensure proper gelation, raise solution pH to 7.4, and removal, of remnant hexane, which has been shown to be cytotoxic over an extended period of time. The capsules could be used immediately or stored in 25 mM CaCl2 at 4° C.

Cell Culture and Encapsulation. Bone Marrow Derived MSCs were cultured with DMEM, (PT-3238, Lonza) until confluent. The cells were trypsin zed, centrifuged, washed, and then mixed with the Ca-EDTA alginate solution at a concentration of $1.5 \times 10^6$ cells $mL^{-1}$. The alginate-cell mixture was then used to form microbeads using the same protocol for clean alginate described above. Encapsulated cells were cultured in DMEM for up to 28 days to assess viability, Live-dead assays (Vybrant CFDA, Invitrogen) were used to measure viability and were performed on days 0, 3, 7, 14, 21, and 28.

Results

Figure 4:
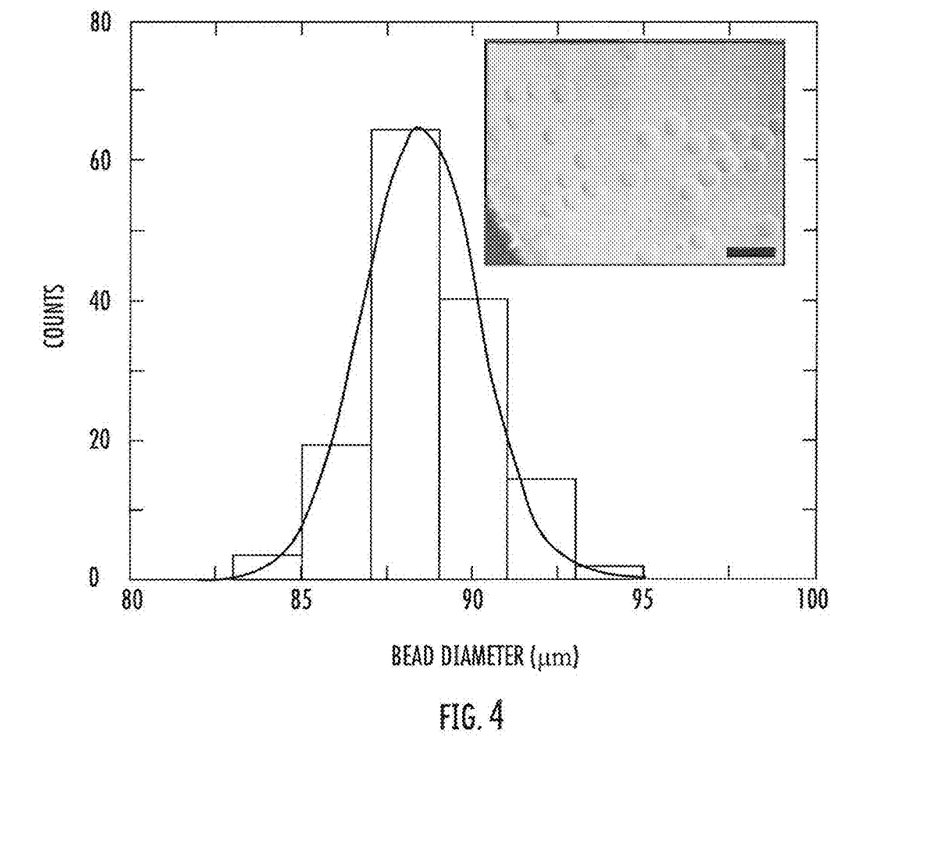
FIG. 4 is a histogram showing the frequency of various bead sizes for a specific flow rate.
Figure 5A:
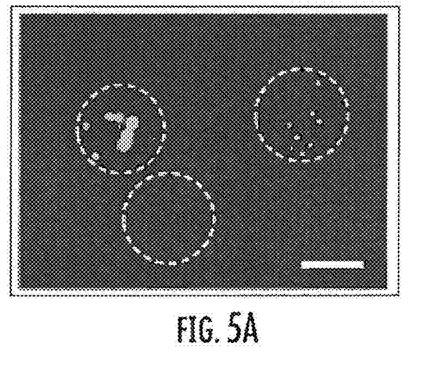
FIGS. 5A-5C show example fluorescent micrographs showing live-dead staining of encapsulated mesenchymal stem cells after (A) 7 days, (B) 14 day, and (C) 28 days, respectively.
Figure 5B:
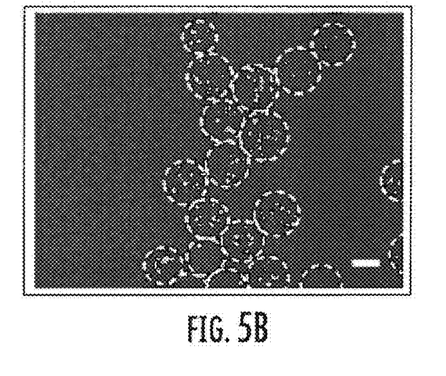
Figure 5C:
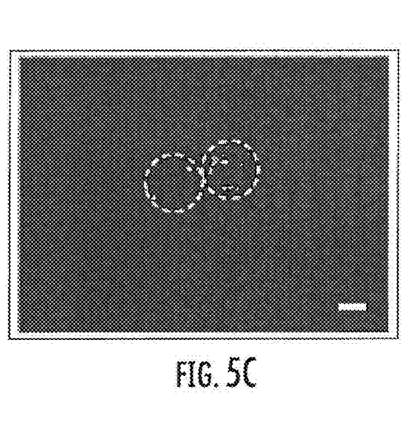
Figure 5D:
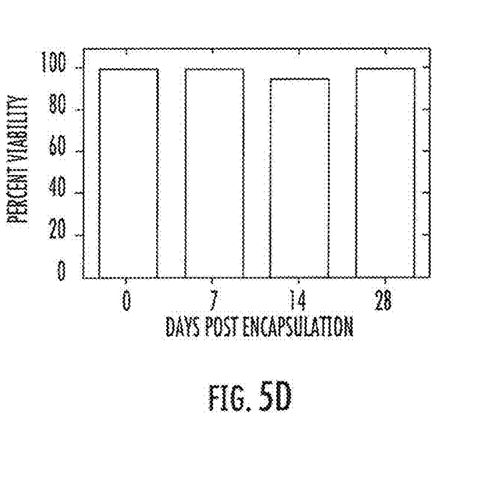
FIG. 5D is a bar graph showing the viability of the encapsulated mesenchymal stem cells of FIGS. 5A-5C over time with day 0 representing mesenchymal stein cells before encapsulation.

Microbead Formation. Droplet size depends on $W_f$; with a larger water fraction, resulting in larger droplets. Therefore increasing or decreasing the oil flow rate can be used to dynamically decrease or increase alginate droplets diameter, respectively. As a metric of monodispersity, we used the coefficient of variance (CV), defined as the ratio of standard deviation to mean diameter. Generally, a population is considered to be monodisperse when CV is less than 5%. The flow rate for chamber 114 is shown in Table 1 while the alginate flow rate is kept constant at 100 μL/hr. With our microfluidic device, we were able to achieve CVs between 2.77% and 5.12% (Table 1), indicating our alginate beads achieved monodispersity under most conditions. We observed that the microbead diameter varied directly with $W_f$, following expectations. FIG. 4 shows a histogram for the best flow parameter we investigated ($W_f$=0.012, CV-2.77%), demonstrating a very sharp Gaussian distribution of bead diameters. A typical bright field image of the microbeads formed under these conditions can be seen in FIG. 4. The flow rates shown are 8 mL/hr, 100 μL/hr, and 8 mL/hr for the 114, 116, and 118 chambers respectively. The average microbead size was 89.72 μm with a coefficient of variance of 2.8% (n=141). The microbeads were analyzed with ImageJ software for surface area, perimeter, circularity, and aspect ratio (scale bar is 100 μm).

Through image analysis, we found a mean area of 7646.19±222.12 $μm^2$ and mean perimeter of 356.98±22.73 μm (n=10). Using these data, we calculated circularity of the microbeads to be 0.86±0.09 and aspect ratio of 1.03±0.02. Therefore, because gelation occurred while surrounded by oil with uniform cross-linker, the beads formed near-perfect spheres that were not distorted by shear forces. For an average bead size of 150 μm and alginate flow rate of 100 μL/hr, bead fabrication occurs at a rate of around 943 beads/min or approximately 15 beads/second. In total, it is clear that the alginate microbeads resulting from our microfluidic device are monodisperse, circular, and reproducible enough for translational applications.

Cell Culture and Encapsulation. Having established an ability to produce highly regular and spherical microbeads, we next incorporated cells in the alginate solution to demonstrate cell encapsulation. For this, we used bone marrow derived MSCs and quantified viability during 28 days in culture. Owing to the change in pH from the crosslinking process, it was particularly important to confirm that the cells remained viable after encapsulation. Using a custom Matlab code, the number of alive and dead cells from across the time course were quantified. The initial cell viability before encapsulation was 99.3%. The cell viability on days 7, 14, and 28 were 100%, 95.7%, and 100% respectively. High viability was thus maintained up to 28 days showing that the encapsulation process was non-toxic (FIGS. 5A-5D). This also demonstrates that adding cells to the alginate does not prevent gelation.

Discussion

Microencapsulation of cells is important for the immunoisolation of allogeneic cells in clinical applications. Polymeric hydrogels such as alginate with perm-selective coatings have been used for encapsulation due to their ability to immobilize and protect cells from the immune system. All microencapsulation devices produce hydrogel beads based on 4 key characteristics; throughput, bead size, sphericity, and monodispersity. A high throughput device is critical in clinical applications where millions of cells are needed for therapeutic efficacy. Decreasing the bead size allows for better nutrient diffusion as well as a reduced inflammatory response if the beads are transplanted directly into tissue. Beads that are more spherical have a decreased risk for macrophage and protein attachment which would reduce the inflammatory response as well. Lastly, monodispersity allows for accurate dosing of cells or therapeutics which is critical when millions of beads are being produced. Spherical, monodisperse beads that are less than 200 µm in diameter are typically made via microfluidic devices, and there is currently limited availability of methods that are capable of producing these beads in a relatively high throughput. This is due to the devices implementing a flow focusing strategy for encapsulation. This is a highly controlled method that involves a dripping of aqueous fluid into a continuous flow of oil. Beads are formed individually and travel in single file along the microfluidic device which is not practical for clinical encapsulation purposes involving millions of cells.

In contrast, our method employs Rayleigh-Plateau instability to generate smooth, small, monodisperse heads in a relatively high throughput manner. The large opening in our device immediately after the alginate-oil junction created a non-laminar flow pattern that increased the shear stress on the alginate as it entered this region. This caused bead formation in a rapid but consistent way through Rayleigh-Plateau Instability which increased the throughput, but not at a sacrifice to the other characteristics, unlike the flow-focusing methods. Once the droplets were rapidly formed, they were focused to another junction containing acidic mineral oil. This drop in caused the EDTA to release $Ca^{2+}$ homogenously throughout the alginate medium. The beads then travel through wide sigmoidal chambers to ensure thorough crosslinking while maintaining the high throughput capacity.

As cell therapy with stem cells gain momentum, the need will arise for encapsulating MSCs direct transplantation into tissue particularly for sustained localized release of therapeutic molecule. Towards such a goal, there would be a need for small, monodisperse alginate microbeads MSCs and prevent them from migrating away from the target tissue for repair, while not inducing an adverse event from the direct transplantation into the tissue. Therefore, a microfluidic device has great potential to achieve success in four key requirements of hydrogel encapsulation for in vivo experiments, namely: throughput, monodispersity size, and sphericity/smoothness. In summary, we have shown that this microfluidic encapsulation process was nontoxic and has been successfully used to encapsulate MSCs that remained viable during a 28-day period of post-encapsulation culture. Thus, our approach has significant potential to enhance the use of encapsulated MSCs for regenerative medicine applications.

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. The invention is defined by the following claims, with equivalents of the claims to be included therein.

TABLE 1

Alginate microbead water fraction, size distribution, and CV.

| Flow Rate (mL/hr) | Water Fraction | Diameter (µm) | CV |
| --- | --- | --- | --- |
| 3 | 0.032 | 180.65 | 4.11% |
| 4 | 0.024 | 124.51 | 5.12% |
| 6 | 0.016 | 131.53 | 3.76% |
| 8 | 0.012 | 89.72 | 2.77% |

That which is claimed is:

1. A method of encapsulating cells using a microfluidic encapsulation device, the microfluidic encapsulation device comprising a first, second, and third flow line, wherein the second flow line junctions the first flow line at a first-second flow line junction, and the third flow line junctions the first flow line at a first-third flow line junction, the first-third flow line junction being at a point after the first-second flow line junction, the method comprising:

flowing an aqueous solution through the first flow line, the aqueous solution comprising alginate homogenously mixed with calcium-ethylenediaminetetraacetic acid (EDTA) and mesenchymal stem cells, wherein the aqueous solution flows through the first flow line at a flow rate in a range of between about 50 µL/hr and about 400 µL/hr;

providing a first non-aqueous liquid comprising mineral oil and a surfactant that flows through the second flow line, the first non-aqueous liquid being immiscible with the aqueous solution, wherein the first non-aqueous liquid flows through the second flow line at a flow rate in a range of between about 3 mL/hr and about 15 mL/hr;

providing a second non-aqueous liquid comprising mineral oil and an acetic acid that flows through the third flow line, the second non-aqueous liquid being immiscible with the aqueous solution, wherein the second non-aqueous liquid flows through the third flow line at a flow rate in a range of between about 4 mL/hr and about 8 mL/hr;

forming an alginate microbead by cutting off the flowing of the aqueous solution with the first non-aqueous liquid at the first-second flow line junction; then lowering a surface pH of the alginate microbead with the second non-aqueous liquid at the first-third flow line junction to initiate crosslinking with the divalent cation and forming a crosslinked alginate microbead, wherein the crosslinked alginate microbead encapsulates the mesenchymal stem cells, thereby encapsulating the mesenchymal stem cells with crosslinked alginate, wherein the method forms a plurality of crosslinked alginate microbeads, wherein the crosslinked alginate microbeads have a monodispersity with a coefficient of variance of less than 5%, and wherein the viability of the encapsulated mesenchymal stem cells is at least 90% for 28 days or more.

2. The method of claim 1, wherein the method further comprises washing the crosslinked alginate microbead with a suitable wash solution.

3. The method of claim 2, wherein the crosslinked alginate microbead is washed with an organic wash solution and/or an aqueous wash solution, and said washing restores the crosslinked alginate microbead to a neutral pH of about 7.0.

4. The method of claim 1, wherein the crosslinked alginate microbead has a diameter of less than 250 μm.

5. The method of claim 1, wherein the crosslinked alginate microbead has a diameter of from about 80 μm to about 180 μm.

6. The method of claim 1, wherein the surface pH of the alginate microbead is lowered at the first-third junction from a neutral pH of about 7.0 to an acidic pH of about 5.0.

7. The method of claim 1, wherein increasing the flow rate of the first non-aqueous liquid through the first flow line decreases the diameter of the alginate microbead.

8. The method of claim 1, wherein the crosslinked alginate microbead has a spherical shape.

9. The method of claim 1, wherein said plurality of crosslinked alginate microbeads are formed at a rate of production from about 100 beads/minute to about 1000 beads/minute.

10. The method of claim 1, wherein the first non-aqueous liquid comprises about 0.1% to about 5% surfactant.

11. The method of claim 1, wherein the second non-aqueous liquid comprises about 0.5% to about 1.5% acetic acid.

12. The method of claim 1, wherein the crosslinked alginate microbeads have a monodispersity with a coefficient of variance between 2.5% and 5%.

13. The method of claim 1, further comprising:
flowing the plurality of crosslinked alginate microbeads with the encapsulated cells through a static mixer.

14. A method of encapsulating cells using a microfluidic encapsulation device, the microfluidic encapsulation device comprising a first, second, and third flow line, wherein the second flow line junctions the first flow line at a first-second flow line junction, and the third flow line junctions the first flow line at a first-third flow line junction, the first-third flow line junction being at a point after the first-second flow line junction, the method comprising:

flowing an aqueous solution through the first flow line, the aqueous solution comprising alginate homogenously mixed with calcium-ethylenediaminetetraacetic acid (EDTA) and mesenchymal stem cells, wherein the aqueous solution flows through the first flow line at a flow rate of about 100 μL/hr;

providing a first non-aqueous liquid comprising mineral oil and about 4% surfactant that flows through the second flow line, the first non-aqueous liquid being immiscible with the aqueous solution, wherein the first non-aqueous liquid flows through the second flow line at a flow rate of about 8 mL/hr;

providing a second non-aqueous liquid comprising mineral oil and about 1.4% acetic acid that flows through the third flow line, the second non-aqueous liquid being immiscible with the aqueous solution, wherein the second non-aqueous liquid flows through the third flow line at a flow rate of about 8 mL/hr;

forming an alginate microbead by cutting off the flowing of the aqueous solution with the first non-aqueous liquid at the first-second flow line junction; then lowering a surface pH of the alginate microbead with the second non-aqueous liquid at the first-third flow line junction to initiate crosslinking with the divalent cation and forming a crosslinked alginate microbead, wherein the crosslinked alginate microbead encapsulates the mesenchymal cells, thereby encapsulating the mesenchymal cells with crosslinked alginate, wherein the method forms a plurality of crosslinked alginate microbeads having a diameter in a range of between about 80 μm and about 180 μm, wherein the crosslinked alginate microbeads have a monodispersity with a coefficient of variance of less than 5%, and wherein the viability of the encapsulated mesenchymal cells is at least 90% for 28 days or more.

* * * * *